United States Patent [19]

Bertagna et al.

[11] 4,347,911

[45] Sep. 7, 1982

[54] ACOUSTIC HEADSET

[75] Inventors: Richard A. Bertagna, San Dimas; Benjamin H. Stansbury, Beverly Hills; Kenneth A. Tarlow, Pacific Palisades, all of Calif.

[73] Assignee: Audio in Motion, Pasadena, Calif.

[21] Appl. No.: 245,127

[22] Filed: Mar. 18, 1981

[51] Int. Cl.³ ............................................... A61B 7/02
[52] U.S. Cl. ...................................... 181/130; 181/131
[58] Field of Search ............... 181/130, 131, 135, 133, 181/134, 129, 132

[56] References Cited

U.S. PATENT DOCUMENTS

| 663,393 | 12/1900 | Price | 181/129 |
|---|---|---|---|
| 2,641,327 | 6/1953 | Balmer | 181/129 |
| 3,493,075 | 2/1970 | Mendelson et al. | 181/131 |
| 3,539,031 | 11/1970 | Scanlon | 181/129 |
| 3,547,219 | 12/1970 | Bothos | 181/135 |
| 4,029,169 | 6/1977 | Huntress | 181/131 X |
| 4,055,233 | 10/1977 | Huntress | 181/135 |
| 4,261,432 | 4/1981 | Gunterman | 181/131 |

Primary Examiner—Donald A. Griffin
Assistant Examiner—Benjamin R. Fuller
Attorney, Agent, or Firm—Christie, Parker & Hale

[57] ABSTRACT

An improved acoustic headset of the type used with sound reproduction equipment in airline entertainment systems. The headset has a yoke supporting a pin of curved sound-transmitting horns which terminate in soft tips for insertion in a passenger's ears. To provide improved alignment with the ear canals, the horns are rotatably mounted on the yoke, and are curved through more than a right angle. The headset provides improved frequency response and comfort to the user, and is designed for easy packaging and cleaning for repeated use.

10 Claims, 8 Drawing Figures

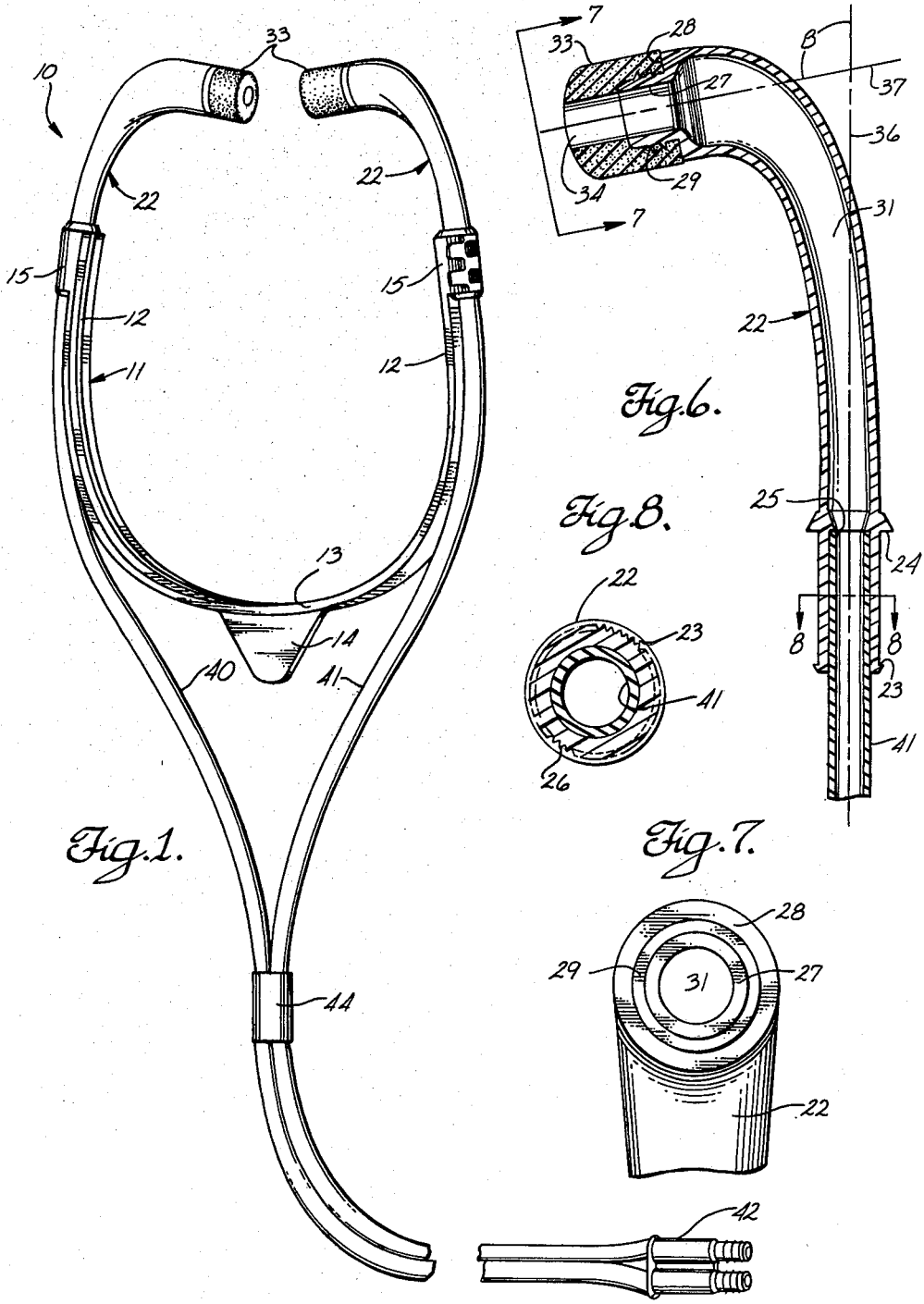

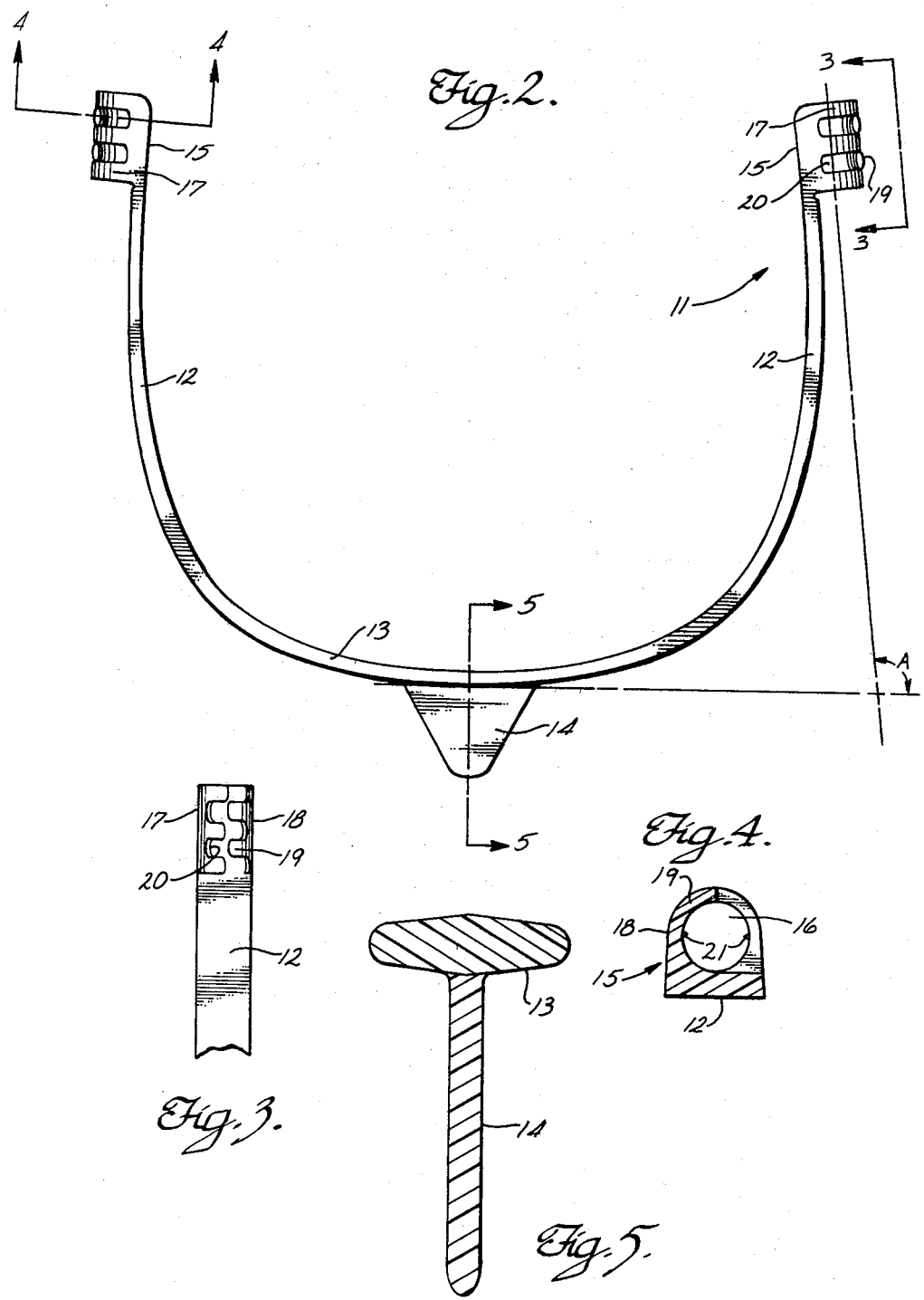

ACOUSTIC HEADSET

BACKGROUND OF THE INVENTION

Passenger entertainment systems are in widespread use in public-transport vehicles such as jet aircraft. These systems include audio equipment for reproducing recorded music or other program material, and the equipment may also be used in conjunction with visual programs presented on a film screen or television display in the passenger compartment of the vehicle.

To enable selective use of the entertainment system, individual earphones are provided to the passengers for plug-in connection to the audio output of the system. Conventional electromagnetic earphones can be used in this application, but acoustic-style headsets are generally preferred for economy, and for simplified cleaning and repackaging enabling re-use of the headset.

An acoustic headset does not include an electromagnetic transducer, and is instead a simple tubing system for conveying sound waves from speakers or similar transducers which are typically located in the passenger's seat. Separate sound tubes enable transmission of two-channel stereo program material, and the tubes terminate in a conventional connector which plugs into a mating receptacle in the passenger's seat.

Acoustic headsets have been used in airline service for many years, but known designs are not completely satisfactory for several reasons. Conventional units are somewhat uncomfortable to wear for long periods of time, and are acoustically inefficient in having poor frequency-response characteristics and improper orientation with respect to the ear canals of the user. These units also have sound-conducting tubes which are supported on the headset yoke in a way which produces sharp bends in the tubing when the headset is packaged. These bends cause kinks in the tubing which further impair the quality of sound transmitted to the user.

Our new design overcomes these problems, and provides an economical multiple-use headset of improved acoustic quality. The new headset uses sound tubing of enlarged diameter as compared to conventional styles, and the tubes terminate in internally tapered horns for further improvement in frequency response. The horns are rotatably mounted on a supporting yoke, and are otherwise configured to enable proper alignment with the typical inwardly downward and forward orientation of human ear canals. The sound tubes are free of mechanical connection to the headset other than at the input ends of the horns, thus permitting the tubing to be neatly coiled without kinks after the unit is cleaned and is ready for repackaging.

SUMMARY OF THE INVENTION

The headset of this invention includes a generally U-shaped yoke having opposed ends, and a pair of hollow sound-conducting horns having first ends adapted for attachment to the yoke ends. Each horn extends from the first end through a bent or curved portion to a second end configured to support an ear-plug tip. A pair of hollow sound-conducting tubes are connected to the first ends of the respective horns, and the opposite ends of the tubes are secured to a plug-in acoustic connector. A mounting means is provided for rotatably anchoring the horn first ends to the yoke ends so the horns can be axially rotated on the yoke.

Preferably, the horns are sufficiently curved that central axes of the opposed horn ends are angularly displaced by more than 90 degrees, and preferably about 102 degrees. This curvature, coupled with the rotatable mounting of the horns on the yoke, enables the output or second ends of the horns to be properly aligned with the user's ear canals. In a presently preferred form, the mounting means is defined by a resilient hollow cylindrical clamp which is integrally formed at each end of the yoke, and a detent means is provided between each clamp and horn so the horns can be indexed into a variety of angular positions.

For improved frequency response and suppression of spurious resonances, the sound-conducting tubes preferably have an inside diameter of about three-sixteenths inch, and the horns have a matching diameter at their input or first ends, the horn inside diameter thereafter increasing exponentially toward the second end. A pair of soft ear-plug tips are fitted over retaining ribs on the horn output ends. The sound-conducting tubes are preferably free of direct connection to the yoke to avoid tube kinking when the headset is packaged, and a nameplate tab is provided at the lower center part of the yoke.

BRIEF DESCRIPTION OF THE DRAWINGS

FIG. 1 is a pictorial view of a headset according to the invention;

FIG. 2 is a front elevation of a yoke for the headset;

FIG. 3 is a side view of a yoke clamp on line 3—3 of FIG. 2;

FIG. 4 is a sectional view of the yoke clamp on line 4—4 of FIG. 2;

FIG. 5 is a sectional view of the yoke on line 5—5 of FIG. 2;

FIG. 6 is a sectional elevation of a horn and cushioned tip as used in the headset;

FIG. 7 is an end view of the horn on line 7—7 of FIG. 6 with the cushioned tip removed; and FIG. 8 is a sectional view of the input end of the horn on line 8—8 of FIG. 7.

DESCRIPTION OF THE PREFERRED EMBODIMENT

A headset 10 according to the invention is shown in FIG. 1, and the headset includes a yoke 11 shown in greater detail in FIGS. 2-5. The yoke is an integrally molded U-shaped member having a pair of opposed arms 12 which are joined at their lower ends by a connecting portion 13. An integral nameplate tab 14 extends downwardly from the center of the connecting portion, and provides a surface for airline identification or the like. The cross-sectional configuration of the yoke is shown in FIG. 5, and this shape is selected to strengthen the yoke against breakage in the event the arms are flexed toward or away from each other by the user.

The upper end of each arm 12 terminates in a resilient clamp 15 having a cylindrical passage 16 therethrough. The clamp is formed by a pair of semi-circular shells 17 and 18 which extend from opposite sides of the arm toward each other to terminate in intermeshing tabs 19 and grooves 20. A pair of axially and radially inwardly extending ribs 21 (FIG. 4) are integrally formed at 180-degree spacing on the inner surfaces of shells 17 and 18.

As shown in FIG. 2, arms 20 are preferably curved at slightly more than a right angle with respect to a horizontal axis of connecting portion 13 of the yoke. This angulation is shown as angle "A" in FIG. 2, and the angle is preferably about 96°. The yoke is preferably molded from a resilient plastic material such as polypropylene.

Headset 10 further includes a pair of hollow sound-conducting horns 22 as shown in FIGS. 1, 6 and 7. The horns are preferably molded as a pair of half-shells from a relatively rigid plastic material such as styrene, and the half-shells are then sonic welded together to form a complete horn.

The lower or input end of each horn has an upwardly facing annular shoulder 23 on its tubular outer surface, and a downwardly facing shoulder 24 on the outer surface of the horn is axially spaced upwardly from shoulder 24. The spacing between these shoulders is selected to match the axial length of clamp 15 on the headset yoke.

The cylindrical inner surface of the lower end of the horn also has an inwardly extending annular shoulder 25 which faces downwardly toward the lower tip of the horn and is axially aligned with shoulder 24. The cylindrical outer surface of the horn input end defines a plurality of axially and radially outwardly extending depressions or serrations 26 (FIG. 8) which are circumferentially spaced apart by six or seven degrees.

The upper or output end of each horn is reduced in cross section to form a sleeve 27. The integral junction of the sleeve and the main body of the horn defines a shoulder 28. A pair of spaced-apart and outwardly extending annular ribs 29 are formed on the outer surfaces of sleeve 27.

The horn is hollow to form a sound-conducting passage 31 of circular cross section and extending between the ends of the horn. Preferably, passage 31 is exponentially tapered to increase in diameter as it extends from shoulder 25 to the junction of the horn with sleeve 27 as shown in FIG. 6. The exponential taper improves the frequency response of the horn, and minimizes spurious resonances in the sound-conducting properties of the headset.

Each horn carries a soft foam-plastic tip 33 which is fitted over sleeve 27 as shown in FIG. 6. The inner end of the tip abuts shoulder 28 on the sleeve, and the tip is retained in position by ribs 29. The tip has a cylindrical passage 34 therethrough, and the diameter of the passage is selected to match the inside diameter of sleeve 27 wich is preferably about 0.220 inch.

The horn is curved to bend through more than a right angle as best seen in FIG. 6. That is, the angulation between a longitudinal axis 36 of the lower end of the horn and a longitudinal axis 37 of the horn sleeve (indicated by angle "B" in FIG. 6) is preferably about 102°.

The headset also includes a pair of sound-conducting plastic tubes 40 and 41 which terminate at one end in a conventional acoustic plug or male connector 42. The other ends of the tubes are fitted into the lower ends of horns 22, and the inward travel of the tube within the horn is limited by inwardly extending shoulder 25. The upper portions of the tubes are not connected to the yoke, but are joined approximately 5 inches below the connecting portion of the yoke by a plastic clip 44.

Prior to installation of sound tubes 40 and 41 in the respective horns, the headset is partially assembled by inserting the lower ends of the horns into clamps 15 on the yoke. Each clamp expands resiliently as the horn is inserted, and then contracts after shoulder 23 has passed through the clamp. Further movement of the horn into the clamp is limited by shoulder 24 which abuts the upper end of the clamp.

Clamp 15 anchors the associated horn against axial movement with respect to the yoke arm, but enables the horn to be rotated with respect to the yoke. This rotational freedom is important, because it enables the axis of the output end of each horn to be more accurately aligned with the axis of the ear canal of the user. Ribs 21 within claim 15 mate with serrations 26 on the outside of the horn input end to provide an indexing action or detent means which retains the horn in a desired rotational position.

The average ear canal extends from its outer end (at the concha of the ear) downwardly and forwardly into the head. The rotational freedom of the horn accommodates the forward orientation of the canal, and the angulation of the horn accommodates the downward orientation of the canal. Sound waves from the horn are thus projected directly down the ear canal to impinge on the eardrum with minimum interference and loss of fidelity.

Tubes 40 and 41 preferably have an outside diameter of about 0.220 inch, and an inside diameter of about 3/16" which corresponds to the diameter of the aperture defined by shoulder 24 within the horn. The horn is internally tapered to expand in diameter as it extends away from shoulder 25 toward sleeve 27, the taper being exponential in curvature to expand the inside diameter to a maximum of about 0.30 inch. The tapered bore of the horn, coupled with the unusually large inside diameter of the sound tubes, contributes to both improved frequency response of the headset, and to suppression of unwanted spurious resonances.

In use, the headset is fitted on the user's head with the cushioned tips resting on the conchae of the ears to block transmission of ambient cabin noise into the ear canals. The horn can then be individually rotated to position the tips for both sound fidelity and comfort. The U-shaped yoke extends under the user's chin, and the sound-tube connector is plugged into the mating receptacle to couple the headset to the entertainment system.

In addition to improved frequency response and reduction of spurious resonances, we have found that the headset of our invention features less attenuation of sound level or volume than in conventional designs. This in turn contributes to improved fidelity of reproduction of the program material, because the playback equipment and electromagnetic transducer which drives the sound tubes can be operated at a lower level, while still maintaining adequate audio volume for the user.

The headset is configured to lie close to the sides of the user's head to avoid interference with adjacent objects when the head is moved. The spacing of the cushioned tips and the resiliency of the yoke are selected such that the tips are urged against the ears with a light and comfortable force of about 3.5 ounces (about 1.75 ounces per side) for an average adult interconchae spacing of about 4.5 to 5.5 inches.

The headset is intended to be recovered by the operator at the conclusion of the entertainment program, and the cushioned tips are removed and replaced with fresh tips. Any necessary cleaning of the headset can be accomplished at this time, and the unit is then repackaged in a plastic envelope for another use. The headset is particularly advantageous in avoiding any direct connection of the sound tubes to the yoke, as this enables the relatively lengthy sound tubes to be coiled neatly around the yoke and horns without introducing any kinks into the sound tubes.

There has been described an improvement entertainment system headset with significantly better frequency response, attenuation, and spurious-resonance characteristics than provided by known units. The headset is economical to manufacture, and is specifically designed for multiple-use applications in transport aircraft and the like.

What is claimed is:

1. An acoustic headset, comprising:
   a generally U-shaped flexible yoke having opposed ends;
   a pair of hollow sound-conducting rigid horns having first ends adapted for attachment to the respective yoke ends, each horn extending from the first end through a curved portion to a second end adapted to support an ear-plug tip, the first and second ends of each horn having central axes which are displaced by an angle of more than 90 degrees, and each horn having an inside diameter which enlarges as the horn extends from the first end toward the second end;
   an acoustic connector having a pair of hollow sound-conducting tubes extending therefrom, the tube ends being connected to the respective first ends of the horns; and
   means for mounting the first ends of the horns to the respective opposed ends of the yoke.

2. The headset defined in claim 1 wherein the mounting means is adapted for rotatably mounting the horns, whereby the horns can be rotated with respect to the yoke to enable improved alignment of the second ends of the horns with ear canals of a user.

3. The headset defined in claim 2 wherein said angle is about 102 degrees.

4. The headset defined in claim 2 wherein the mounting means is a clamp integrally formed at each of the opposed ends of the yoke.

5. The headset defined in claim 2 wherein the sound-conducting tubes have an inside diameter of about three-sixteenth inch.

6. The headset defined in claim 5 wherein the first end of each horn defines an inwardly extending shoulder having an inside diameter of about three-sixteenth inch, the inside diameter of the hollow horn enlarging exponentially as the horn extends toward the second end.

7. The headset defined in claim 2, and further comprising a pair of resilient ear-plug tips fitted on the second ends of the respective horns.

8. The headset defined in claim 2 wherein the tubes are free of direct attachment to the yoke.

9. The headset defined in claim 2, and further comprising a detent means between each horn first end and the associated mounting means to retain the horn in a desired rotational position.

10. The headset defined in claim 9, wherein said angle is about 102 degrees, wherein the mounting means is a clamp integrally formed at each of the opposed ends of the yoke, wherein the sound-conducting tubes have an inside diameter of about three-sixteenths inch and each horn has an inside diameter which enlarges exponentially toward the second end, and wherein the tubes are free of direct connection with the yoke.

* * * * *